US012642564B2

(12) United States Patent
Flavin

(10) Patent No.: US 12,642,564 B2
(45) Date of Patent: Jun. 2, 2026

(54) SCREW CAPTURE SYSTEM FOR CALCANEAL FRACTURE

(71) Applicant: RLFA Consultants Ltd, Dublin (IE)

(72) Inventor: Robert Flavin, Enniskerry (IE)

(73) Assignee: RLFA Biomedical Ltd, Sandyford (IE)

( * ) Notice: Subject to any disclaimer, the term of this patent is extended or adjusted under 35 U.S.C. 154(b) by 0 days.

(21) Appl. No.: 18/727,073

(22) PCT Filed: Aug. 30, 2023

(86) PCT No.: PCT/IB2023/000523
§ 371 (c)(1),
(2) Date: Jul. 6, 2024

(87) PCT Pub. No.: WO2024/047400
PCT Pub. Date: Mar. 7, 2024

(65) Prior Publication Data
US 2025/0072943 A1 Mar. 6, 2025

Related U.S. Application Data

(60) Provisional application No. 63/402,962, filed on Sep. 1, 2022.

(51) Int. Cl.
A61B 17/72 (2006.01)

(52) U.S. Cl.
CPC ........ A61B 17/7291 (2013.01); A61B 17/725 (2013.01)

(58) Field of Classification Search
CPC ............ A61B 17/7291; A61B 17/7216; A61B 17/7225; A61B 17/7233; A61B 17/725
See application file for complete search history.

(56) References Cited

U.S. PATENT DOCUMENTS

2005/0101958 A1*  5/2005  Adam .................... A61B 17/72
                                          606/62
2005/0165395 A1*  7/2005  Orbay ................ A61B 17/8061
                                          606/60

(Continued)

FOREIGN PATENT DOCUMENTS

CN          204274612          4/2015
CN          109009378          12/2018

(Continued)

OTHER PUBLICATIONS

PCT/IB2023/000523 International Search Report. Feb. 6, 2024.
PCT/IB2023/000523 International Preliminary Report on Patentability.

*Primary Examiner* — Julianna N Harvey
(74) *Attorney, Agent, or Firm* — Joseph E. Maenner; Maenner & Associates, LLC

(57) ABSTRACT

A screw capture system for calcaneal repair is provided. The system includes an elongate nail having a hollow body with a longitudinal axis extending through the body and a through passage extending along the longitudinal axis. The body has a plurality of through-openings formed therein transverse to longitudinal axis, each of the plurality of through-openings defined by an internal wall. At least one support post is sized to be inserted into each of the plurality of through-openings. At least one set screw is inserted into the through passage. Each of the at least one set screw biases one of the at least one support posts against the internal wall of the respective through-opening.

17 Claims, 8 Drawing Sheets

(56)     References Cited

U.S. PATENT DOCUMENTS

| | | | | |
|---|---|---|---|---|
| 2008/0183171 A1 * | 7/2008 | Elghazaly | .......... | A61B 17/7241 |
| | | | | 606/301 |
| 2008/0221577 A1 * | 9/2008 | Elghazaly | .......... | A61B 17/7241 |
| | | | | 606/62 |
| 2008/0294164 A1 * | 11/2008 | Frank | .................. | A61B 17/744 |
| | | | | 606/301 |
| 2011/0160729 A1 * | 6/2011 | Overes | ............... | A61B 17/7241 |
| | | | | 606/286 |
| 2017/0252076 A1 * | 9/2017 | Boraiah | ............. | A61B 17/7225 |
| 2023/0098345 A1 * | 3/2023 | Vicenzi | ............. | A61B 17/7225 |
| 2023/0240729 A1 * | 8/2023 | Eceviz | ............... | A61B 17/7291 |
| | | | | 606/62 |

FOREIGN PATENT DOCUMENTS

| | | | | |
|---|---|---|---|---|
| DE | 202022100295 | | 3/2022 | |
| KR | 20220040287 | | 3/2022 | |
| WO | WO-2021185971 A1 * | 9/2021 | ......... | A61B 17/7225 |

* cited by examiner

SCREW CAPTURE SYSTEM FOR CALCANEAL FRACTURE

BACKGROUND OF THE INVENTION

Field of the Invention

The invention relates to a system that is used to capture screws that are used to repair a calcaneal fracture.

Description of the Related Art

Present procedures to repair calcaneal fractures entail large destructive expansile incisions that include a double incision, which can lead to wound complications and possible nerve damage.

It would be beneficial to provide a repair system that reduces the number, as well as the size of the incision, and reduces the likelihood of wound complications, such as infection, as well as possible nerve damage.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a screw capture system for calcaneal repair. The system includes an elongate nail having a hollow body with a longitudinal axis extending through the body and a through passage extending along the longitudinal axis. The body has a plurality of through-openings formed therein transverse to longitudinal axis, each of the plurality of through-openings defined by an internal wall. At least one support post is sized to be inserted into each of the plurality of through-openings. At least one set screw is inserted into the through passage. Each of the at least one set screw biases one of the at least one support posts against the internal wall of the respective through-opening.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
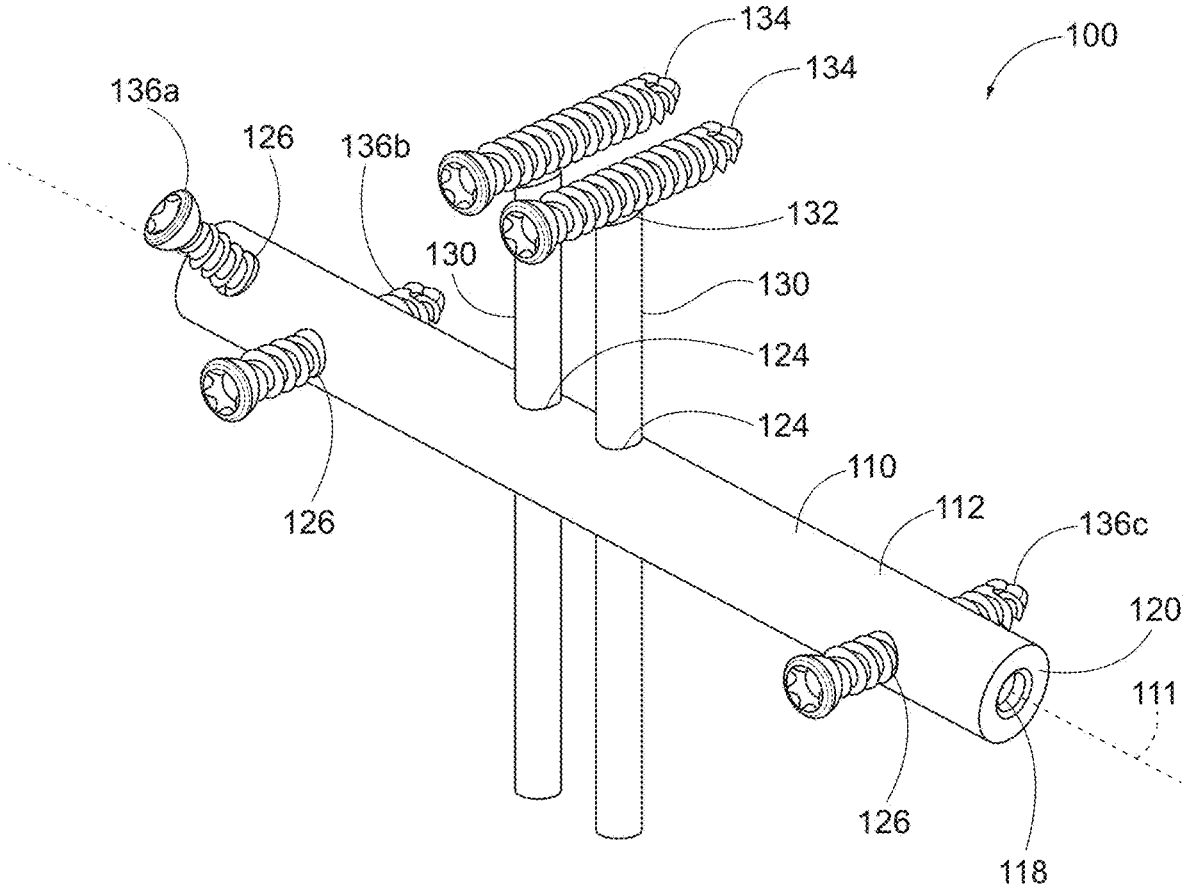
FIG. 1 is a perspective view of a screw nail capturing system according to an exemplary embodiment of the present invention.
Figure 2:
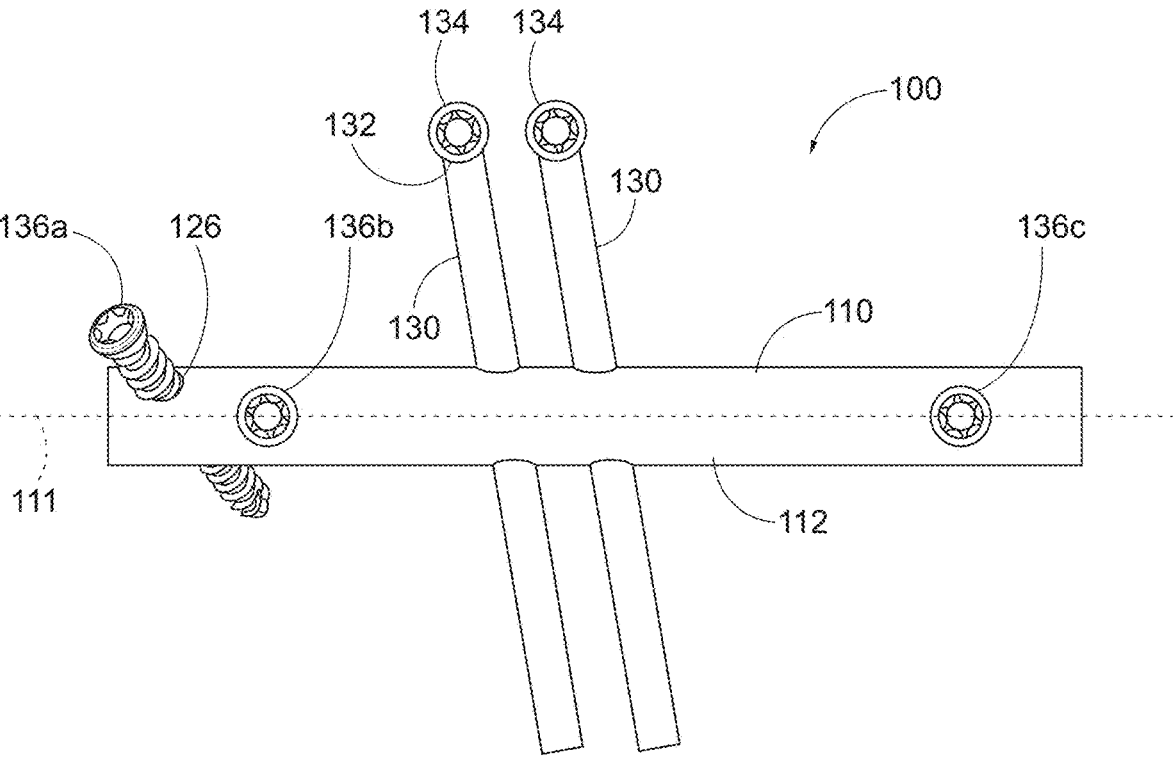
FIG. 2 is a side elevational view of the system of FIG. 1.
Figure 3:
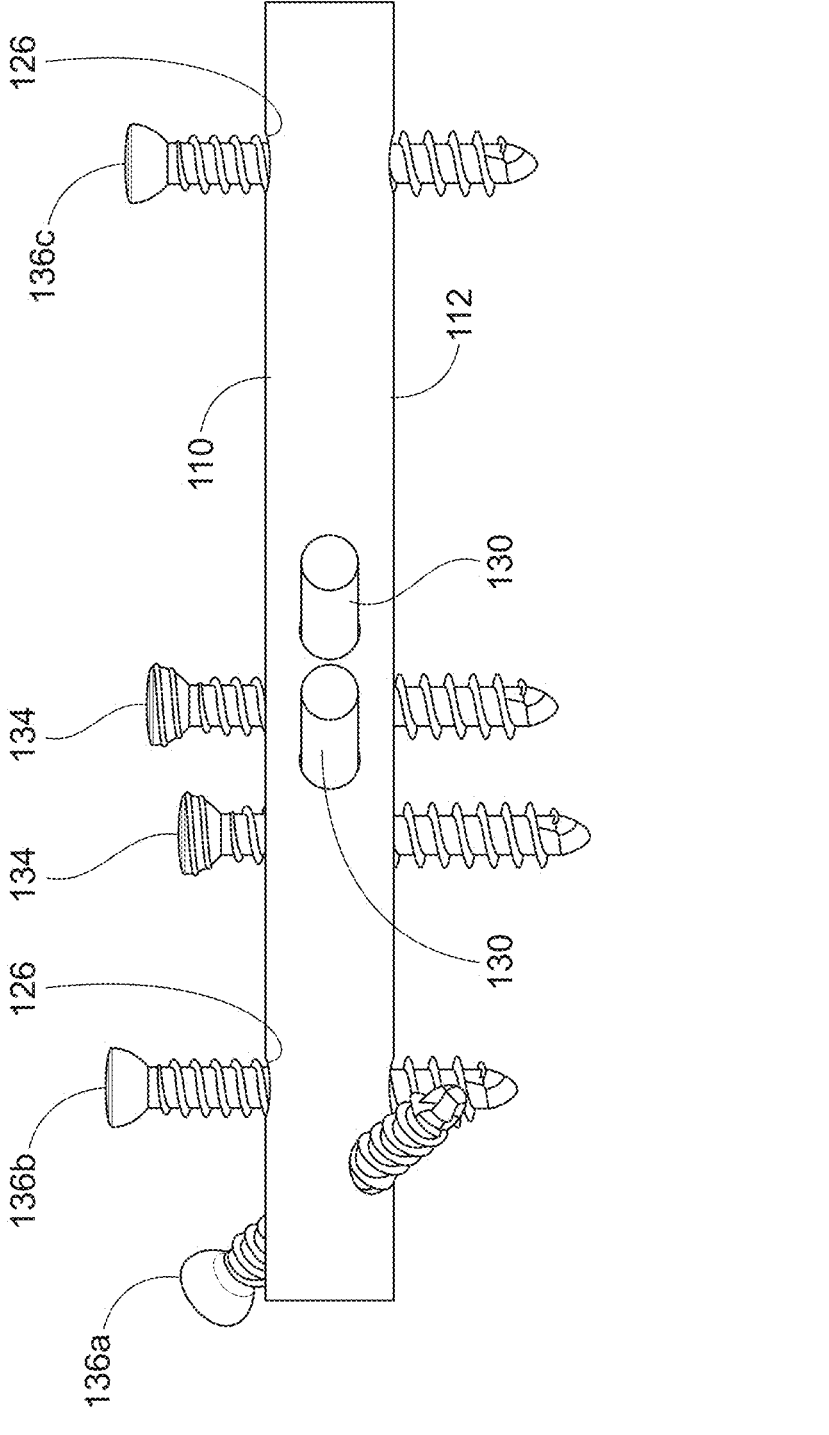
FIG. 3 is a top perspective view of the system of FIG. 1.
Figure 4:
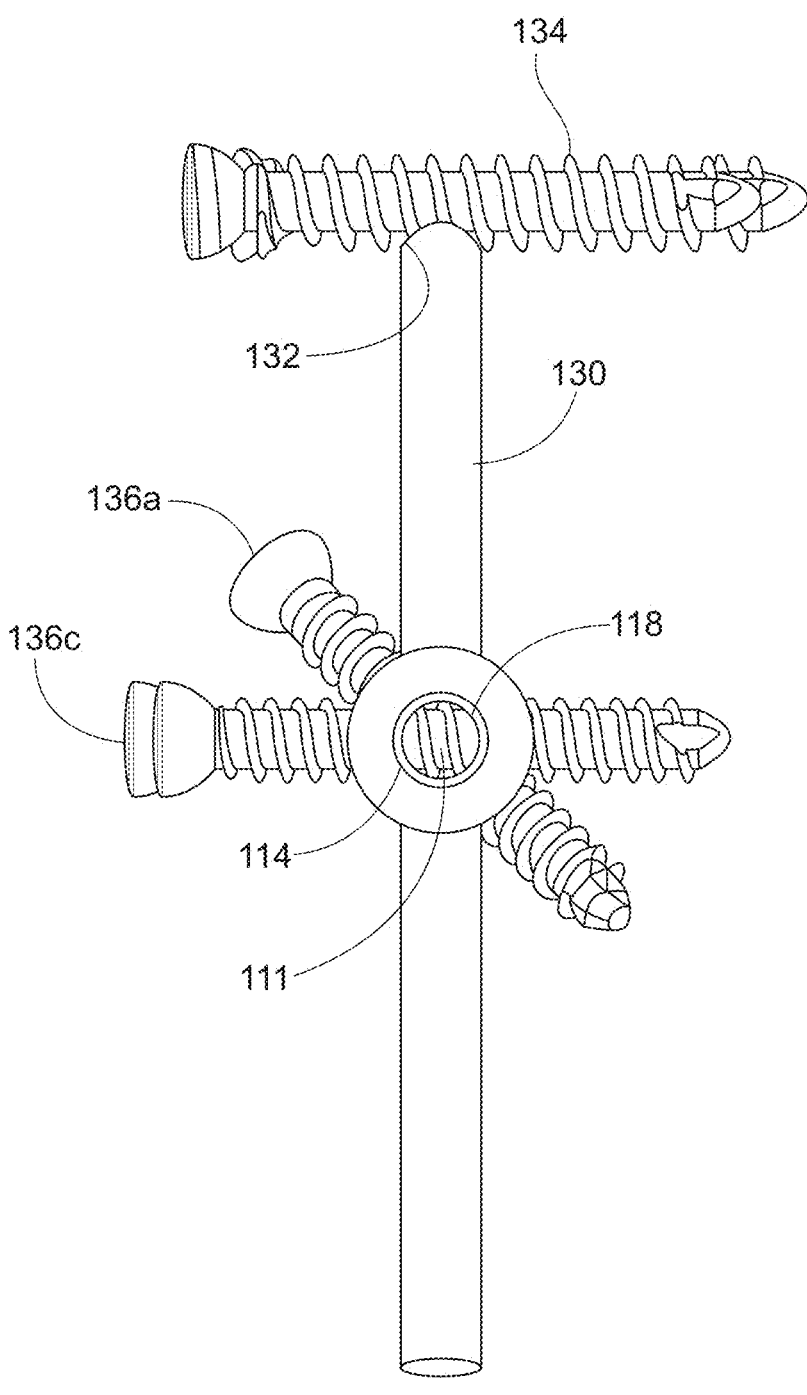
FIG. 4 is a perspective view of the system of FIG. 1 used on a tibia.

U.S. Provisional Patent Application Ser. No. 63/402,961, entitled "Ligament/Tendon Suture with Paired Anchor System", invented by this inventor; U.S. Provisional Patent Application Ser. No. 63/402,965, entitled "Screw Blade Capture System", invented by this inventor; U.S. Provisional Patent Application Ser. No. 63/402,967, entitled "Repair Plate System from Inside/Out", invented by this inventor; U.S. Provisional Patent Application Ser. No. 63/402,964, entitled "Talar Repair Jig", invented by this inventor; U.S. Provisional Patent Application Ser. No. 63/402,971, entitled "Syndesmosis Repair Jig Assembly and Method of Use", invented by this inventor; U.S. Provisional Patent Application Ser. No. 63/402,969, entitled "Distal Tibial Osteotomy System", and invented by this inventor; and U.S. Provisional Patent Application Ser. No. 63/402,963, entitled "External Fixation System", invented by this inventor, and all filed on Sep. 1, 2022, are all incorporated herein by reference in their entireties.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Figure 5:
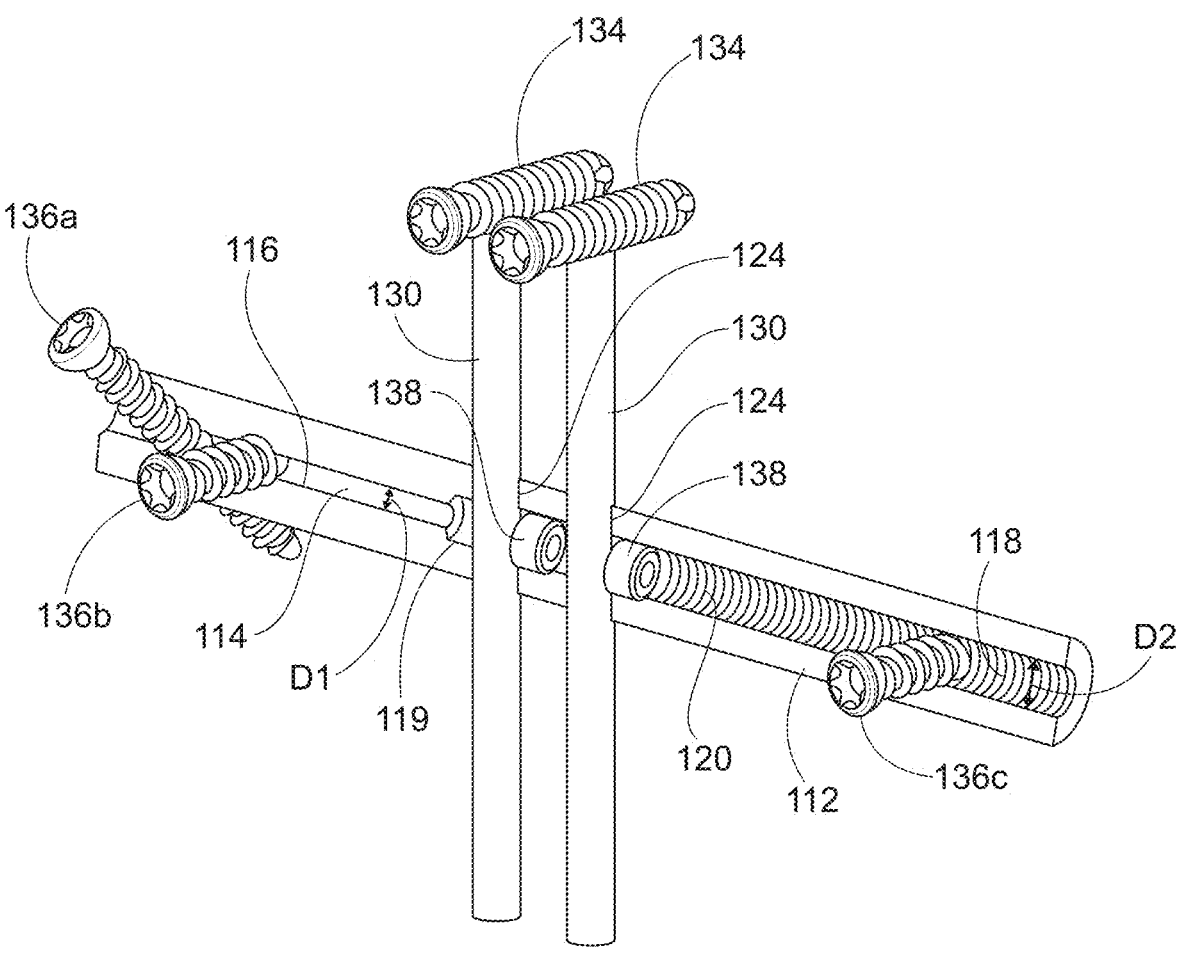
FIG. 5 is a side elevational view of the system of FIG. 1 attached to the tibia of FIG. 4.
Figure 6:
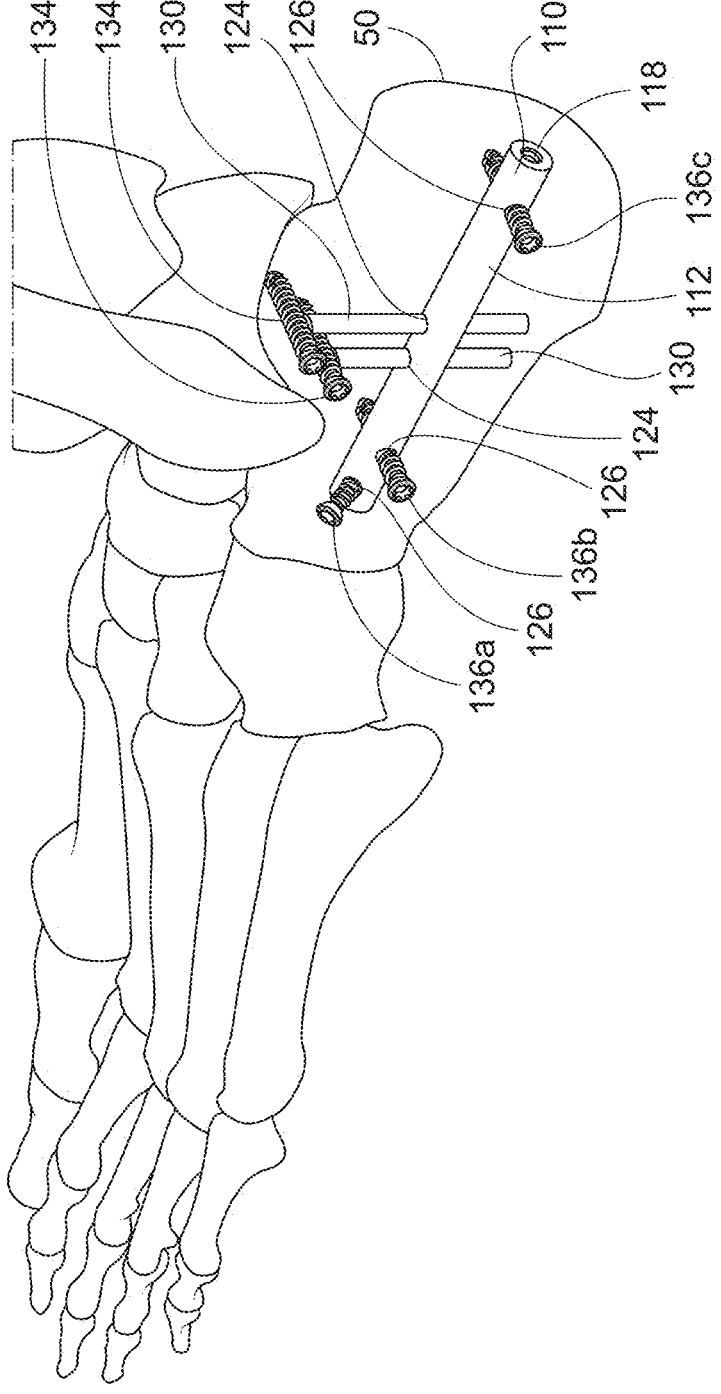
FIG. 6 is a top perspective view of the system of FIG. 1 attached to the tibia of FIG. 4.

The present invention is a system for providing a support structure for repair of a fractured calcaneus 50 (shown in FIG. 6). Referring to FIGS. 1-5, a screw capture system 100 ("system 100") for such a repair according to an exemplary embodiment of the present invention is shown. System 100 is beneficial in supporting repair screws that are used to attach fractured or otherwise damaged calcaneal bone portions together, to prevent fracture fixation collapse.

System 100 includes an elongate nail 110 having a hollow body 112 with a through passage 114 extending therethrough. In an exemplary embodiment, nail 110 can be selected from a plurality of nails 110 having differing lengths, such as between about 60 mm and about 100 mm, as well as differing diameters, such as between about 6 mm and about 10 mm.

A longitudinal axis 111 extends longitudinally through body 110. Through passage 114 has an anterior portion 116 and a posterior portion 118. Anterior portion 116 has a first diameter D1 and posterior portion 118 has a second diameter D2, larger than D1. A lip 119 defines a junction between anterior portion 116 and posterior portion 118. Also, posterior portion 118 is threaded with internal threads 120.

A plurality of through-openings 124, 126 are formed in body 112 transverse to longitudinal axis 111 Nail 110 is implanted after a cannulated reamer (not shown) forms a canal after the fracture is reduced. The nail 110 is inserted with the through-openings 124, 126 having been made during the manufacturing process. Through-openings 126 are formed at an angle relative to through-openings 124.

A first subset of through-openings 124 are formed through posterior portion 118 of through passage 114 and are sized to allow minimal threaded support posts 130 to be inserted therethrough. Support posts 130 are used to support fixation screws 134 that do not extend through body 112, but are required to secure bone fragments of the posterior facet of the calcaneus 50 together. Support posts 130 can be longitudinally adjusted in nail 110 depending on the distance between nail 110 and the respective fixation screw 134. Also, each support post 130 includes a saddle 132 to support their respective fixation screw 134. Although two support posts 130 are shown, those skilled in the art will recognize that more or less than two support posts 130 can be used. Additionally, while fixation screws 134 are shown as being supported by support posts 130, those skilled in the art will recognize that support posts 130 can support other elements as well.

As seen in FIG. 5, set screws 138 are used to secure support posts 130 with respect to body 112. After an anterior-most support post 130 is inserted through body 112, a first set screw 138 is threaded along internal threads 120 to bias and secure that support post 130 against the internal wall of its respective through-opening 124. Next, the posterior-most support post 130 is inserted through body 112, a second set screw 138 is threaded along internal threads 120 to bias and secure that support post 130 against the internal wall of its respective through-opening 124.

Fixation screws 136a, 136b, 136c can be inserted through a second subset of through-openings 126 to secure bone fragments of calcaneus 50 together. All screws are inserted with an outrigging jig connected to the Nail 110.

4

Figure 7:
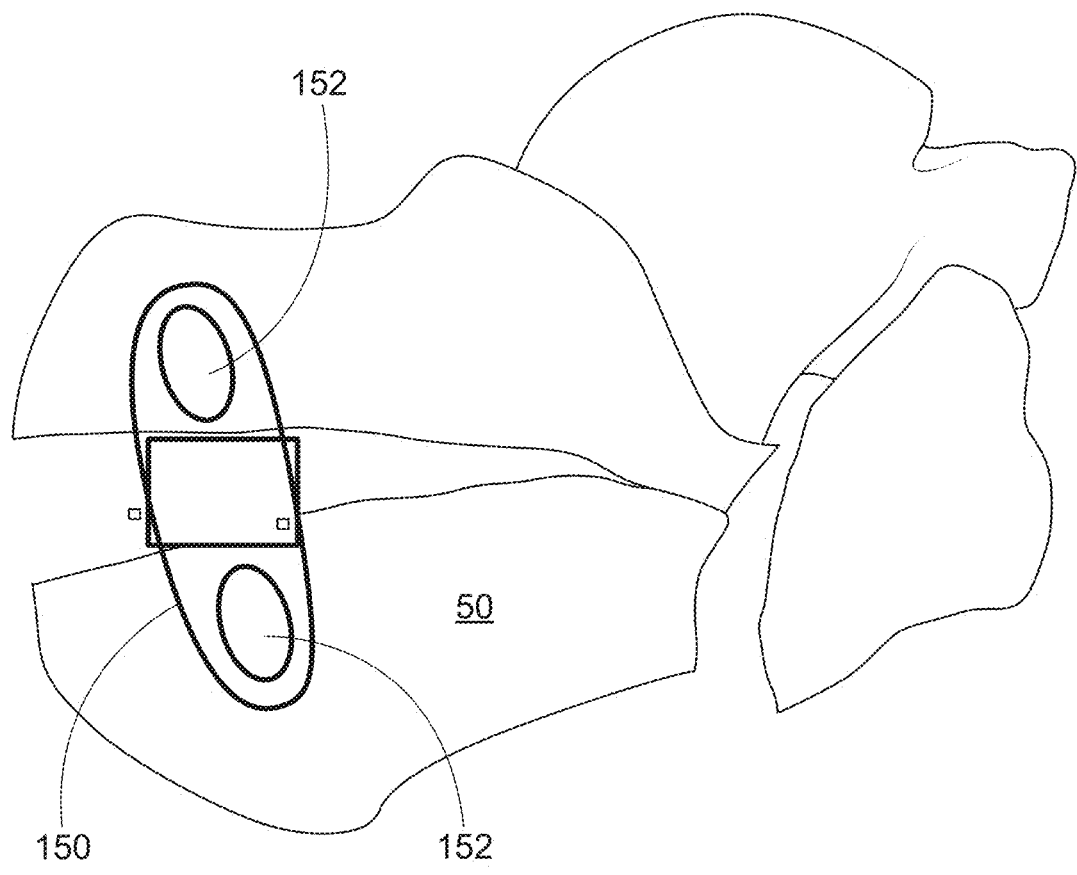
FIG. 7 is a side elevational view of a plate used with the screw nail capturing system of FIG. 1 attached to a fractured calcaneus.
Figure 8:
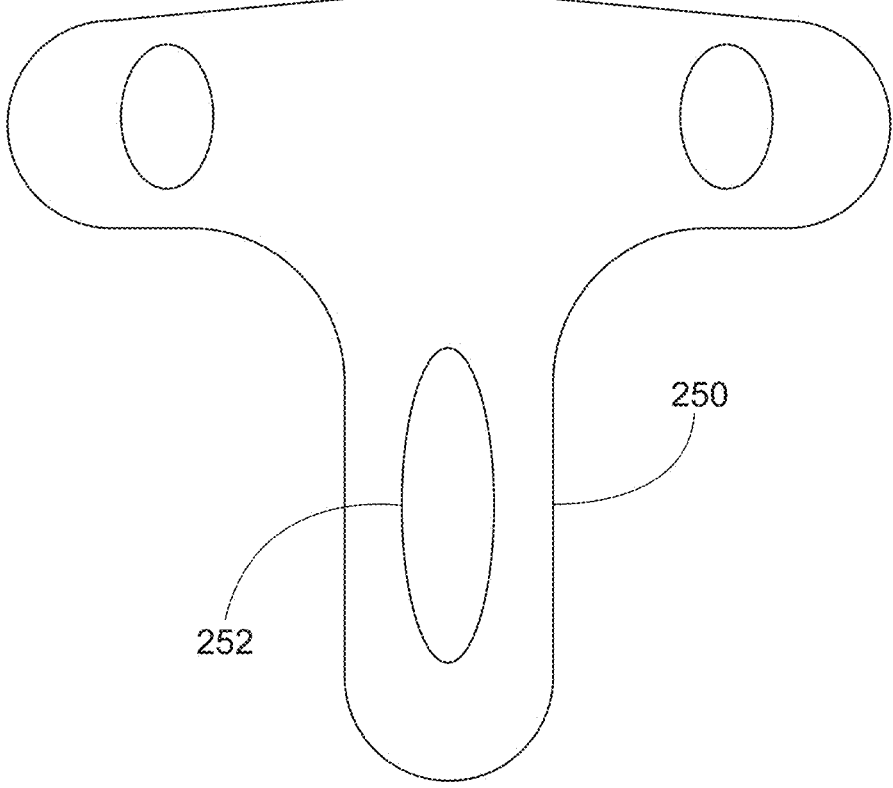
FIG. 8 is a side elevational view of an alternative embodiment of a plate used with the screw nail capturing system of FIG. 1.

Referring to FIGS. 7 and 8, fracture plates 150, 205 are provided to sit on the lateral surface of the calcaneus 50 in the case of a "tongue-type" fracture. The fracture plate 150, 250 can either be straight (150) or T-shaped and has an oblong hole 152, 252 to be captured by screw 136b to address tongue-type fractures of the calcaneus 50. Plates 150, 250 are inserted through a separate vertical calcaneal tuberosity incision (not shown).

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A screw capture system for calcaneal repair, the system comprising:
   an elongate nail having a hollow body with a longitudinal axis extending through the body and a through passage extending along the longitudinal axis, the body having a plurality of through-openings formed therein transverse to longitudinal axis, each of the plurality of through-openings defined by an internal wall;
   at least one unthreaded support post sized to be inserted into each of the plurality of through-openings; and
   at least one set screw inserted into the through passage, wherein each of the at least one set screw biases one of the at least one support posts against the internal wall of the respective through-opening,
   wherein each of the at least one unthreaded support post includes an open faced saddle at an end thereof configured to support threads on a respective fixation screw.

2. The screw capture system according to claim 1, wherein the through passage has an anterior portion and a posterior portion.

3. The screw capture system according to claim 2, wherein the anterior portion has a first diameter and the posterior portion has a second diameter larger than the first diameter.

4. The screw capture system according to claim 2, wherein the through passage comprise a lip defining a junction between the anterior portion and the posterior portion.

5. The screw capture system according to claim 2, wherein the posterior portion is threaded with internal threads.

6. The screw capture system according to claim 5, wherein the at least one set screw is screwed into the internal threads.

7. The screw capture system according to claim 2, wherein a first subset of the plurality of through-openings are formed through the posterior portion.

8. The screw capture system according to claim 7, wherein the at least one support post extends through the each of the first subset of the plurality of through-openings.

9. The screw capture system according to claim 8, wherein the fixation screws do not extend through the body.

10. The screw capture system according to claim 7, wherein a second subset of the plurality of through-openings are formed through the anterior portion.

11. The screw capture system according to claim 10, further comprising fixation screws configured for insertion through each of the second subset of the plurality of through-openings.

12. The screw capture system according to claim 10, wherein each of the second subset of the plurality of through-openings extends along an axis at an angle relative to the at least one support post.

13. The screw capture system according to claim 1, wherein each of the at least one support post is longitudinally adjustable in each respective through-opening.

14. A screw capture system for calcaneal repair, the system comprising:

an elongate nail having a hollow body with a longitudinal axis extending through the body and a through passage extending along the longitudinal axis, the body having a plurality of through-openings formed therein transverse to longitudinal axis, each of the plurality of through-openings defined by an internal wall;

a first unthreaded support post sized to be inserted into a first of the plurality of through-openings;

a second unthreaded support post sized to be inserted into a second of the plurality of through-openings, the second unthreaded support post being substantially parallel to the first unthreaded support post; and a set screw inserted into the through passage, wherein the set screw biases the first unthreaded support post against the internal wall of the first of the plurality of through-openings, such that the set screw is located between the first unthreaded support post and the second unthreaded support post, wherein each of the first and second unthreaded support posts have an open-faced saddle at an end thereof configured to support threads on a respective fixation screw.

15. The screw capture system according to claim 14, wherein the set screw is in direct contact with the first unthreaded support post to secure the first unthreaded support post against an internal wall of the first of the plurality of through-openings.

16. A screw capture system for calcaneal repair, the system comprising:

an elongate nail having a hollow body with a longitudinal axis extending through the body and a through passage extending along the longitudinal axis, the body having a plurality of through-openings formed therein transverse to longitudinal axis, each of the plurality of through-openings defined by an internal wall;

a first unthreaded support post sized to be inserted into a first of the plurality of through-openings;

a second unthreaded support post sized to be inserted into a second of the plurality of through-openings; and a first set screw inserted into the through passage, wherein the first set screw is in direct contact with the first unthreaded support post to secure the first unthreaded support post against an internal wall of the first of the plurality of through-openings; and a second set screw inserted into the through passage, wherein the second set screw is in direct contact with the second unthreaded support post to secure the second unthreaded support post against an internal wall of the second of the plurality of through-openings, wherein each of the first and second unthreaded support posts have an open-faced saddle at an end thereof configured to support threads on a respective fixation screw.

17. The screw capture system according to claim 16, wherein the second unthreaded support post extends through the elongate nail between the first set screw and the second screw.

* * * * *